United States Patent [19]

Berzofsky et al.

[11] Patent Number: 5,283,323
[45] Date of Patent: Feb. 1, 1994

[54] METHOD OF PRODUCING IMMUNE RESPONSE

[75] Inventors: Jay A. Berzofsky, Bethesda, Md.; Hajime Kawamura, Tochigi, Japan

[73] Assignee: The United States of America as represented by the Department of Health and Human Services, Washington, D.C.

[21] Appl. No.: 715,712

[22] Filed: Jun. 18, 1991

Related U.S. Application Data

[63] Continuation of Ser. No. 338,362, Apr. 13, 1989, abandoned, which is a continuation of Ser. No. 763,218, Aug. 7, 1985, abandoned.

[51] Int. Cl.$^5$ .................. A61K 39/00; C07K 13/00
[52] U.S. Cl. .................. 530/387.1; 530/387.3; 530/391.7; 424/85.91
[58] Field of Search .............. 424/85.8, 85.91, 88; 435/7.1, 7.2, 942; 436/547, 819, 823; 530/350, 387.9, 387.1, 391.1; 514/885

[56] References Cited

U.S. PATENT DOCUMENTS

| | | | |
|---|---|---|---|
| 4,520,226 | 5/1985 | Neville et al. | 424/85 |
| 4,608,251 | 8/1986 | Mia | 424/85 |
| 4,647,655 | 3/1987 | Axen | 530/390 |
| 4,664,911 | 5/1987 | Uhr et al. | 424/85 |
| 4,689,311 | 8/1987 | Weltman | 435/7 X |
| 4,695,624 | 9/1987 | Marburg | 530/395 |
| 4,704,366 | 11/1987 | Juarez-Salmons et al. | 436/548 X |

OTHER PUBLICATIONS

Boyd et al., 1985, J. Immunol., 134(3);1516.
Tony & Parker, 1985, J. Exp. Med., 161:223.
Lanzavecchia, 1985, Nature, 314:537.
Vitetta et al., 1983, Science, 219:644.
Ramakrishnon & Hanston, 1985, Cancer Res., 45:2031.
Blythman et al., 1981, Nature, 290:145.
Rock et al., J. Exp. Med., vol. 160, Oct. 1984, pp. 1102–1113.
Lanzavecchia, A., Nature, vol. 314, Apr. 11, 1985, pp. 537–539.
Rock, K. L., et al., (1984), J. Exp. Med., 160, 1102–1113.
Sege et al., "Use of Anti-idiotypic Antibodies as Cell-surface Receptor Probes", Proc. Natl. Acad. Sci., USA, vol. 75, (May 1978), pp. 2443–2447.
Kennedy et al., "Immune Response to Hepatitis B Surface Antigen: Enhancement by Prior Injection of Antibodies to the Idiotype", Science, vol. 221, (Aug. 1983), pp. 853–855.
Celis et al., "Antibodies to Hepatitus B Surface Antigen Potentiate the Response of Human T Lymphogate Clones to the Same Antigen", Science, vol. (Apr. 1984), pp. 297–299.
Celis et al., "Regulation of T-cell Function by Antibodies: Enhancement of the Response of Human T-cell Clones to Hepatitis B Surface Antigen by Antigen-specific Monoclonal Antibodies", Proc. Natl. Acad. Sci. USA, vol. 81, (Nov. 1984), pp. 6846–6850.
Casten et al., "Anti-immunoglobulin Augments the B-cell Antigen—Presentation Function Independently of Internalization of Receptor-Antigen Complex", Proc. Natl. Acad. Sci. USA, vol. 82, (Sep. 1985), pp. 5890–5894.
Stoner et al., "Enhanced Antitoxin responses in Irradiated Mice Elicited by Complexes of Tetmus Toxoid and Specific Antibody", J. Immunol., vol. 91, (1963), pp. 761–770.

(List continued on next page.)

Primary Examiner—Robert J. Hill, Jr.
Assistant Examiner—K. Cochrane Carlson
Attorney, Agent, or Firm—Birch, Stewart, Kolasch & Birch

[57] ABSTRACT

The present invention discloses a process for enhancing antibody response to an antigen. A novel step in the process is the preparation of a conjugate of the antigen with an anti-immunoglobulin. The conjugate thus prepared is then administered to a host for in vivo effect or presented to T and B cells in a suitable culture system for in vitro response. The present invention by increasing immunogenicity makes it possible to produce antibodies against very low doses of antigens and otherwise weak or insufficient antigens or synthetic vaccines.

15 Claims, 10 Drawing Sheets

OTHER PUBLICATIONS

Unanue, "Antigen-Presenting Function of the Macrophage", *Ann. Rev. Immunol.*, vol. 12, 1984, pp. 395–428.

Terres, et al., "Enhanced Immunological Sensitization of Mice by the Simultaneous Injection of Antigen and Specific Antiserum", *J. Immunol.* vol. 86, (1961), pp. 361–368.

Lanzauecchia, "Antigen-specific Interaction between T and B Cells", *Nature*, vol. 314, (Apr. 1985), pp. 537–539.

Chesnut, et al., "Antigen Presentation by Normal B Cells, B Cell Tumors and Macro Phages: Functional and Biochemical Comparison", *J. Immunol.*, vol. 128, No. 4, (1982), pp. 1764–1768.

Erlanger, "Principles and Methods for the Preparation of Drug Protein Conjugates for Immunological Studies", *Pharmacological Reviews*, vol. 25, No. 2, (1973), pp. 271–280.

Mitchison, "Antigen Binding and T Cells", *Nature*, vol. 320, (Mar. 1986), pp. 106–107.

Biochemistry, Chapter 7, "Protein Function and Evolution", 1990, pp. 248–254, by Mathews et al.

Journal of Experimental Medicine, vol. 156, Sep. 1982, pp. 791–809, "Genetic Control . . . Myoglobins", by Kohno et al.

The Journal of Immunology, vol. 128, No. 4, Apr. 1982, "Idiotypes of Anti-Myoglobin Antibodies . . . ", by Kohno et al.

The Journal of Immunology, vol. 145, No. 11, pp. 3594–3600, Dec. 1, 1990, "Rapid Stimulation of Large . . . Antibody", by Lees et al.

METHOD OF PRODUCING IMMUNE RESPONSE

This application is a continuation, of application Ser. No. 07/338,362 filed on Apr. 13, 1989, now abandoned which is a continuation of application Ser. No. 06/763,218, filed Aug. 7, 1985, now abandoned.

BACKGROUND OF THE INVENTION

1. Technical Field

The present invention is related to immunology. More particularly, the present invention is related to producing improved immune response to an antigen by targeting the antigen to the immune system.

2. State of the Art

Immunogenicity of antigens in vivo or their potency in vitro is dependent on several factors. Important among such factors are the characteristics of the antigen itself and of the host. Molecular properties of the antigen itself might include: (a) size of the antigen, correlated with the number of antigenic determinants; (b) affinity for functional structures of cells in the immune system, such as immunoglobulins on B cells, cell surface membranes of antigen-presenting cells, Ia molecules after being processed, or T cell receptors with Ia molecules; or (c) susceptibility or resistance to lysosomal enzymes. In the whole animal, the distribution, catabolism, and excretion of the injected antigen also influence the magnitude of immune response. Of course, the route of administration, use of adjuvants, and antigen dosage are some other factors which influence the fate of antigen and the immune response.

Despite rapid advances in immunology, a problem in inducing protective immunization or producing an effective vaccine is faced when the antigens are either too weak or too limited in quantity to be used as immunogens. The present invention now overcomes this limitation in immunology and provides a means of achieving enhanced immune response to an antigen by targeting the antigen to the immune system thereby inducing improved antigenic potency for an otherwise weaker entity.

Several studies have shown that B cells can function as antigen-presenting cells. These fall into three categories. First, at relatively high antigen concentration, B cells and B cell tumors have been shown to take up antigen nonspecifically and to present it to T cells (Chesnut, et al. *J. Immunol.* 128:1764, 1982). For small resting B cells, this function is much more radiosensitive than for accessory cells (AC); such as, dendritic cells [Steinman, et al. *J. Exp. Med.* 149:1, 1979] or macrophages) (Ashwell, et al. *J. Exp. Med.* 159:881, 1984). Second, antigen-specific B cells have shown to take up antigen efficiently at low concentration via their specific surface immunoglobulin and to stimulate specific T cells (Rock, et al. *J. Exp. Med.* 160:1102, 1984; Malynn, et al. *J. Immunol.* 132:2253, 1984). This mechanism is probably the most physiological type of B cell presentation, but it is difficult to purify antigen-specific B cells experimentally. Third, advantage has been taken of using xenogeneic anti-immunoglobulin antibodies as an antigen (Chesnut, et al. *J. Immunol.* 126:1075, 1981; Tony, et al. *J. Exp. Med.* 161:223, 1985). These antibodies can bind to all B cells, but bind with high affinity as in the second approach, and so are presented more effectively than the corresponding xenogeneic immunoglobulin not specific for B cell surface Ig. Thus, this third approach combines some of the advantages of each of the other two approaches; however, so far this approach has been useful only for stimulating T cells specific for xenogeneic immunoglobulin. The present invention now makes it possible to direct any antigen towards the immune system and determine its effect on immunogenicity.

SUMMARY OF THE INVENTION

It is, therefore, an object of the present invention to provide a method of enhancing antigenic potency in vitro and immunogenicity in vivo.

It is a further object of the present invention to produce an improved antigenic response in a host by targeting the antigen to the immune system.

Other objects and advantages of the present invention would become apparent as the detailed description of the present invention proceeds.

BRIEF DESCRIPTION OF THE DRAWINGS

These and other objects, features and many of the attendant advantages of the invention will be better understood upon a reading of the following detailed description when considered in connection with the accompanying drawings wherein.

DETAILED DESCRIPTION OF THE INVENTION

Figure 1:
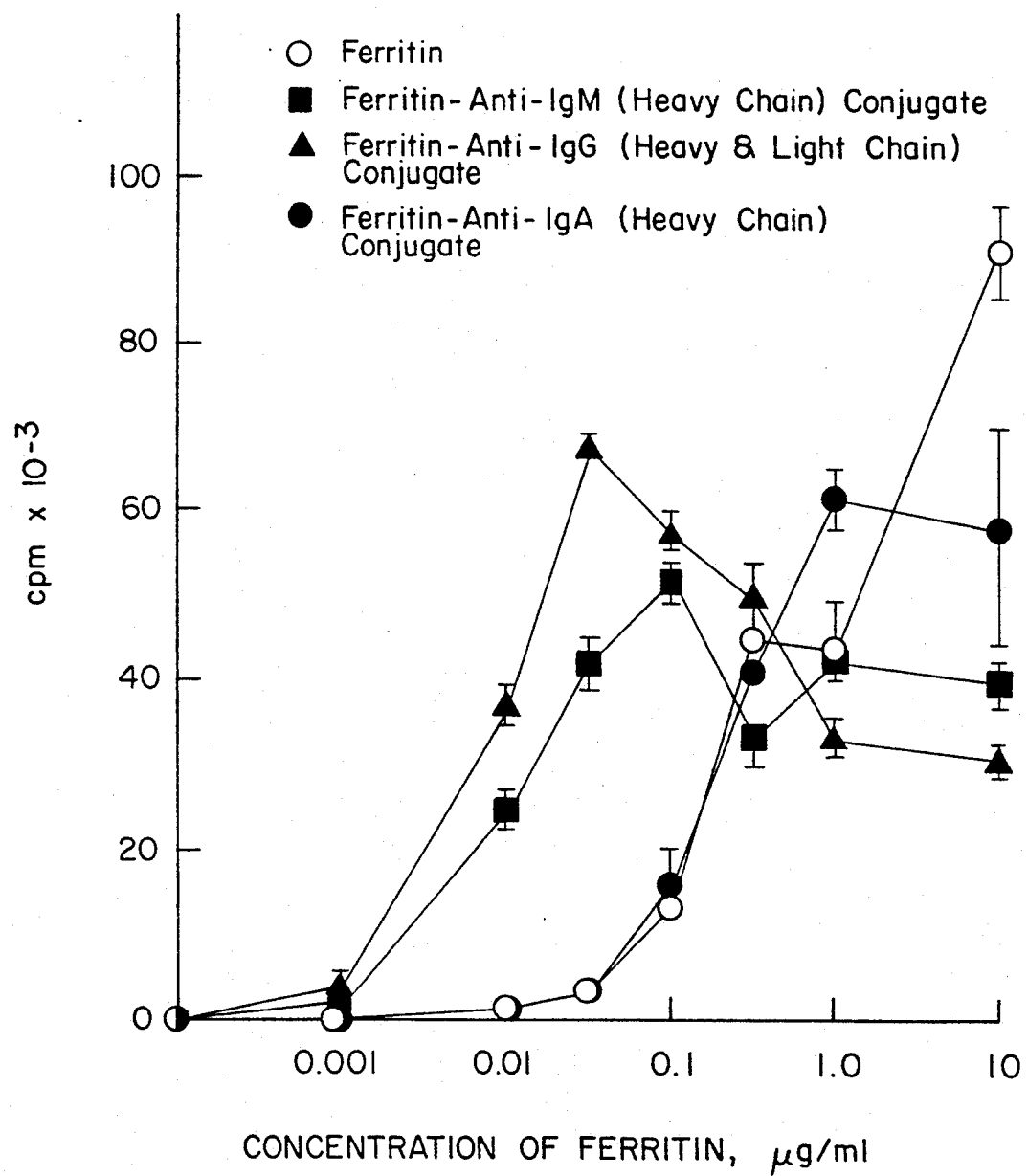
FIG. 1 shows the effect of coupling antigen with anti-immunoglobulin antibodies on its potency for T cell stimulation. A ferritin-specific T cell line ($5 \times 10^3$/well) was cultured for 4 d with 1000 rad-irradiated spleen cells ($5 \times 10^4$/well) in the presence of ferritin (O) ferritin-anti-IgM (H) ■ , ferritin-anti-IgG (H+L) (▲), or ferritin-anti-IgA (H) (●) at the concentration indicated on the abscissa. Error bars are SEM of triplicate cultures.

The above objects and advantages of the present invention are achieved by providing a method of enhancing in vivo antibody production to an antigen comprising cross-linking said antigen with an anti-immunoglobulin to produce a conjugate thereof and then administering suitable amount of said conjugate to a host.

Although any similar or equivalent materials and methods can be employed for the practice of the present invention or for the tests mentioned herein, the preferred materials and methods are now described. All publications listed hereunder are incorporated herein by reference.

MATERIALS AND METHODS

Mice. B10.D2/nSn, B10.BR/SgSn, and B10.A/SgSn mice were obtained from the Jackson Laboratories, Bar Harbor, Me. Mice were about 8 to 16 weeks old at the first immunization.

Antigens. Anti-immunoglobulin which can be used is not limited to those mentioned herein. The anti-immunoglobulin may be monoclonal or polyclonal and may be specific to heavy or light chain immunoglobulin or to mixture of heavy and light chain immunoglobulin. Furthermore, the immunoglobulin may belong to any one of various classes, e.g. IgG, IgM, IgD and the like.

Horse ferritin was a six-times crystallized preparation from Miles Laboratories, Elkhart, Ind. Ferritin-conjugated IgG goat anti-mouse IgG (heavy and light chain specific), IgM (heavy chain specific), or IgA (heavy chain specific) antibodies were obtained from Cappel Laboratories, Inc., West Chester, Pa. The molar substitution of ferritin to immunoglobulin determined by Cappel was 3 (13.1 mg/mg) and was confirmed by the enzyme-linked immunoabsorbent assay (ELISA). The concentrations of ferritin were determined from absorbance at 440 nm at pH 7.2 using an extinction coefficient for ferritin at 1 mg/ml of $A_{440} = 1.56$. The concentration or dose specified in the cultures or for priming is that of the ferritin moiety. Mouse γ-globulin fraction II was obtained from Miles Laboratories, Elkhart, Ind.

Beef myoglobin was purified from heart muscle by the method of Hapner et al. *J. Biol. Chem.* 243:683, 1968, and the major chromatographic component IV was used in these studies. The major chromatographic component IV of sperm whale myoglobin was prepared as described by Berzofsky, *J. Immunol.* 120:360, 1978. These antigens are only examples. The method described herein could be applied to virtually any antigen, and is not limited to those antigens mentioned.

Antibodies. Alkaline-phosphatase-conjugated goat anti-mouse immunoglobulin and IgG goat anti-mouse IgG (heavy and light chain specific) were from Cappel Laboratories, Inc., West Chester, Pa. Affinity-purified mouse anti-horse ferritin (Lockland, Gilbertsville, Pa.) was used in the ELISA as a concentration standard.

Establishment of a Ferritin-specific T Cell Line and a Beef Myoglobin-specific T Cell Line. The procedure of Kimoto and Fathman, *J. Exp. Med.* 152:759, 1980, as modified by Matis et al. *J. Immunol.* 130:1527, 1983 and Berkower et al. *J. Immunol.* 132:1370, 1984, was used. In accordance with this procedure, B10.D2 mice were immunized in the foot pads with 100 μg of ferritin or beef myoglobin in complete Freund's adjuvant. Seven days later, draining lymph nodes were removed and single cell suspensions were passed through a nylon wool column, and the purified T cells were incubated at $4 \times 10^6$ cells/well with $2 \times 10^6$ irradiated syngeneic spleen cells and ferritin 10 μg/ml or beef myoglobin at 2 μM in long-term growth medium. Four days later, responding T cell blasts were harvested from the wells and purified from dead cells by Ficoll density gradient centrifugation. The T cells were then put in resting culture at $4 \times 10^5$ cells/well with $4 \times 10^6$ irradiated spleen cells for 10 days without antigen. Then $5 \times 10^6$ irradiated spleen cells plus antigen were added to begin another round of stimulation and rest. After three to four rounds, most cells of the line were antigen specific as judged by loss of activity for alloantigens and other protein antigens.

Cell Preparation. Presenting-cell populations were prepared from spleen cells from unprimed mice and irradiated with various doses from a $^{137}$Cs source. For the preparation of macrophages, spleen cells were treated with rabbit anti-mouse brain-associated antigen antiserum (obtained from Drs. Richard Hodes and Yoshi Asano, National Cancer Institute, National Institutes of Health) and guinea pig complement (GIBCO, Grand Island, N.Y.) to deplete T cells. After T cell depletion, splenic glass-adherent cells were obtained by the method of Kohno, et al. *J. Immunol.* 128:2458, 1982. Then the glass-adherent cells were incubated on a goat anti-mouse IgM (Fc portion specific, Cappel Lab.)-coated plastic dish (Falcon 3025, Oxnard, Calif.) for 1 h at 4° C. (low temperature to prevent SAC adherence), and nonadherent cells were harvested and used as splenic accessory cells (SAC). Sephadex G-10 passed B cells were prepared by a modification of the method described by Ly and Mishell, *J. Immunol. Meth.* 5:239 (1974) and Hodes et al. *J. Immunol.* 121:1501 (1978). Thus, T cell-depleted spleen cells were incubated 90 min at 37° on glass Petri dishes and nonadherent cells were further incubated on a Sephadex G-10 column for 45 min at 37° C. and eluted with warmed medium. This procedure was repeated three times, and cells which did not bind to the Sephadex G-10 column were used as G-10-column passed B cells.

T Cell Proliferation Assay. Five thousand T cells were incubated in 96-well flat-bottomed microtiter plates (Costar, Cambridge, Mass.), with different presenting-cell populations and antigen in a final volume of 0.2 ml. Assays were performed in the complete medium for T cell lines mentioned above. After 72 h, except for the kinetic study, the cultures were pulsed with 1 μCi/well of tritiated thymidine (New England Nuclear, Boston, Mass.) and harvested 16 h later. Cultures were performed in triplicate, and the data were expressed as the arithmetic mean and standard errors of the mean.

Immunization for In Vivo Antibody Production. Mice were injected subcutaneously at the base of the tail with antigen emulsified in incomplete Freund's adjuvant (Difco Laboratories, Detroit, Mich.; total volume 50 μl). Sera were obtained by bleeding from the tail vein on the days indicated.

Determination of Antibody Production In Vivo. Antibody production was measured by ELISA by a modification of the techniques described by Voller et al. In Manual of Clinical Immunology. 2nd ed. pp. 359–371 (1980) and Murphy et al. *J. Clin. Microbiol.* 13:554 (1981). Accordingly, serum samples, which were titrated at several dilutions, were incubated for 2 h at room temperature on disposable polystyrene plates (Dynatech Laboratory, Inc., Alexandria, Va.) coated with ferritin or sperm whale myoglobin. One hundred microliters of alkaline-phosphatase-conjugated goat anti-mouse immunoglobulin antibodies was added to each well after unbound material was washed out. The plates were incubated for 2 h at room temperature and washed, and the amount of alkaline phosphatase bound to the well was determined by measuring the hydrolysis of p-nitrophenyl phosphate (Sigma Chemical Co., St. Louis, Mo.) to the yellow product, p-nitrophenolate, which was quantitated by absorbance at 405 nm. The optical density was converted to micrograms antibody by means of a standard curve based on a reference affinity-purified mouse antiferritin serum or a reference B10.D2 antimyoglobin serum, which had been independently assayed by a solution radiobinding assay (Berzofsky, 1978. *J. Immunol.* 120:360). Data obtained from the immuno-assay were calculated with the log-logit formulation described by Rodbard and Hutt (In Radioimmuno-assay and Related Procedures in Medicine. Vol. 1., pp. 165–192) using a computer program written by Dr. Robert Yarchoan, National Cancer Institute, National Institutes of Health) for a Wang 2200 computer (Wang Laboratories, Lowell, Mass.).

Effect of Coupling Antigen to Anti-immunoglobulin Antibodies on the Potency for Stimulation of Antigen-specific T Cells In Vitro. The activity of ferritin, ferritin coupled to goat anti-mouse IgM (heavy chain) (H), ferritin coupled to goat anti-mouse IgG (heavy and light chain( (H+L), and ferritin coupled to goat anti-mouse IgA (heavy chain) (H) to stimulate the ferritin-specific T cell line to proliferate in the presence of 1000 rad-irradiated unseparated spleen cells were compared. As shown in FIG. 1, ferritin, coupled to goat anti-mouse IgM (H) or goat anti-mouse IgG (H+L) was capable of stimulating the ferritin-specific T cell line at a concentration at least 10-fold lower than the free ferritin or ferritin coupled to goat anti-mouse IgA (H) antibodies. This effect was not simply due to the coupling of ferritin to some carrier protein since ferritin coupled to goat anti-mouse IgA did not show the enhanced antigenicity. The goat antibodies to different mouse isotypes were themselves of the same isotype (IgG).

The effect of coupling ferritin to the appropriate anti-mouse immunoglobulin was seen over the entire 5-day time course of the response studied. Therefore, coupling ferritin to anti-IgM or anti-IgG (H+L) did not simply change the kinetics of T cell response.

Specificity of the Enhancement Effect of Coupling Anti-IgM or Anti-IgG to the Antigen. Without being bound to any specific theory, a simple explanation for the observed effects may be that the anti-IgM or anti-IgG (H+L) coupled to ferritin focuses the antigen with high affinity onto Ig receptors of B cells. The high affinity binding alone might account for the presentation at lower concentrations. These B cells then process and present ferritin to T cells. However, in addition, the B cells are more prevalent than SAC in the spleen cell population. The larger number of Ia-positive cells that can serve as presenting cells may decrease the threshold concentration for antigen to stimulate T cells, as suggested by Matis et al. *Proc. Natl. Acad. Sci. USA* 80:6019 (1983). Alternatively, the binding of anti-immunoglobulin to surface immunoglobulin on B cells may activate B cells to become more efficient nonspecific presenting cells similar to SAC. To test this latter possibility, free ferritin was mixed with an equivalent or larger amount of anti-IgG (H+L) compared with the ferritin anti-IgG conjugate and was tested for its activity to stimulate T cells in the presence of 1000 rad-irradiated spleen cells.

Figure 2:
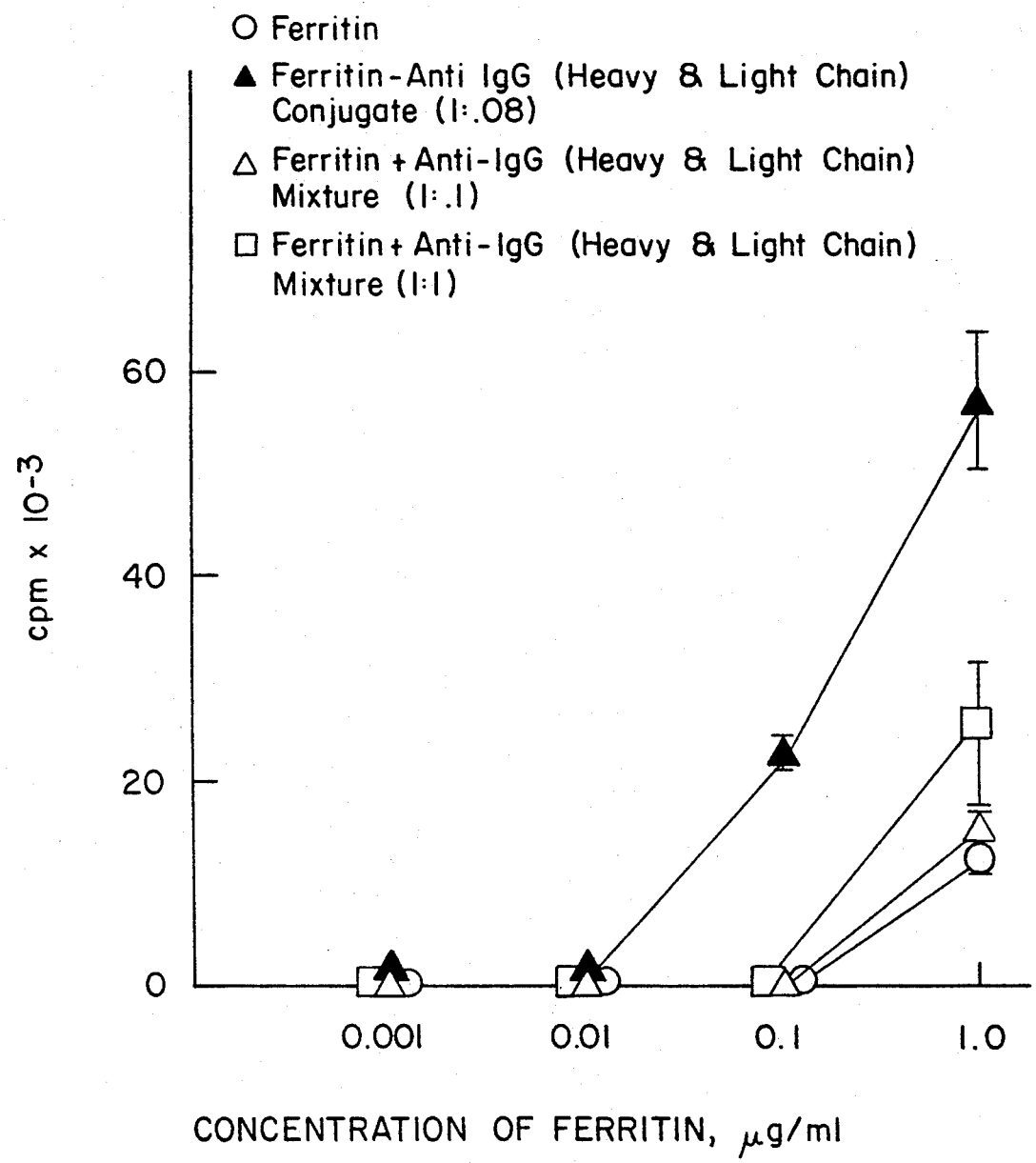
FIG. 2 shows comparison of the effects of free anti-IgG (H+L) and coupled anti-IgG (H+L) on the proliferative T cell response to ferritin. A ferritin-specific T cell line ($5 \times 10^3$/well) was cultured in the presence of ferritin (O), ferritin-anti-IgG (H+L) (ferritin, µg/ml : anti-IgG, µg/ml=1:0.076▲, or ferritin plus anti-IgG (H+L) (ferritin, µg/ml : anti-IgG, µg/ml=1:0.1,△, or 1:1,□) with 1000 rad-irradiated spleen cells ($5 \times 10^4$/well) for 4 d. Error bars are SEM of triplicate cultures. Note that the 1:0.1 ratio is comparable to the conjugate, whereas 1:1 is a 10-fold excess of anti-Ig.
Figure 3:
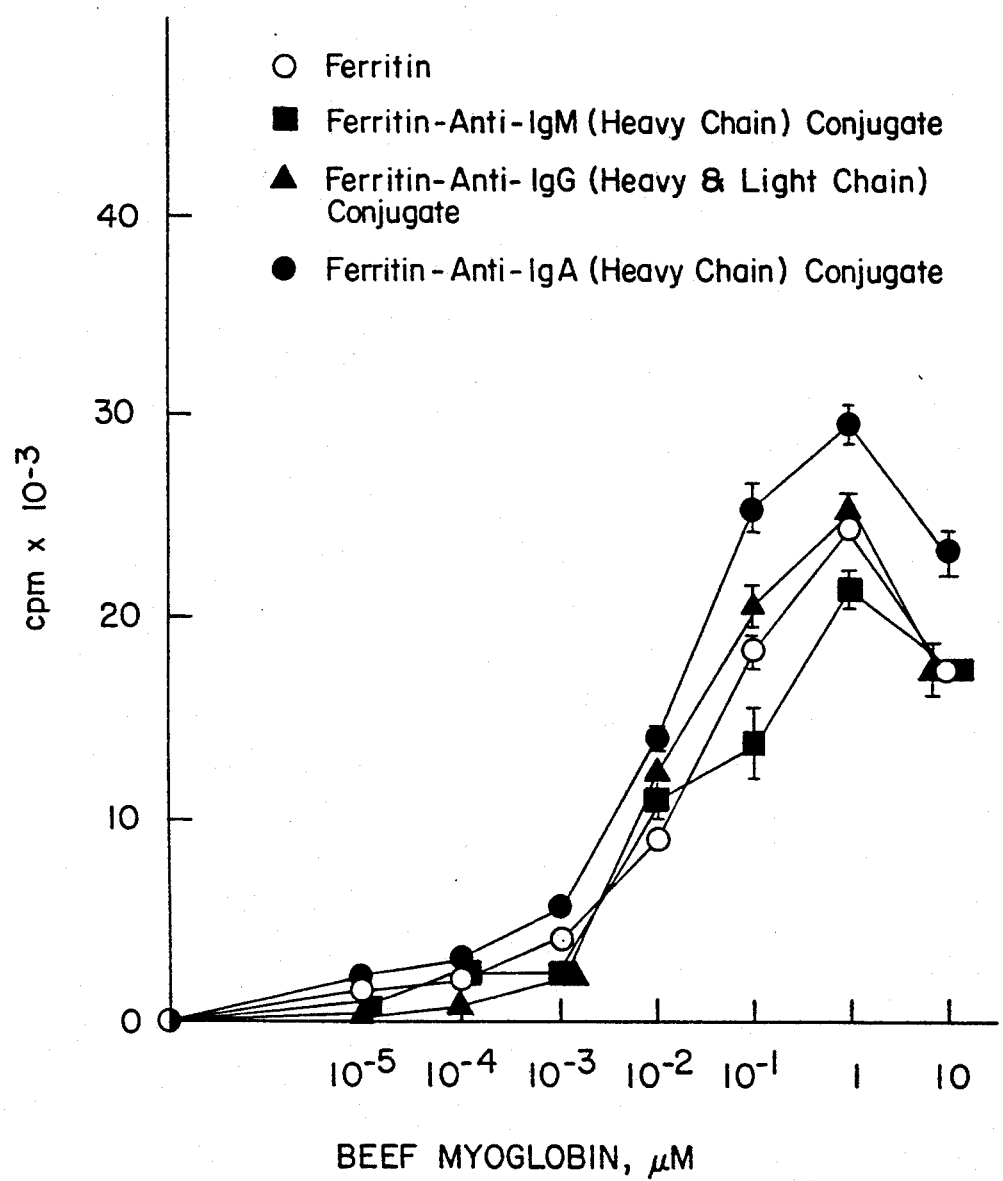
FIG. 3 shows the influence of ferritin conjugates on response of T cells specific for unrelated antigen. A beef myoglobin-specific T cell line ($5 \times 10^3$/well) was cultured with 1000 rad-irradiated spleen cells ($5 \times 10^4$/well) plus beef myoglobin at the concentration indicated on the abscissa together with 0.05 µg/ml of ferritin (O), ferritin-anti-IgM (H) (■), ferritin-anti-IgG (H+L) (▲), or ferritin-anti-IgA (●) for 4 d. Error bars are SEM of triplicate cultures. This experiment was done with FIG. 5, which serves as the positive control, showing the different potency of 0.05 µg/ml of ferritin and ferritin conjugates to stimulate ferritin-specific T cells.

The mixture of ferritin and anti-mouse IgG did not stimulate better than ferritin alone, although with a 10-fold higher amount of anti-mouse IgG a small enhancement of T cell proliferation was seen (FIG. 2). Furthermore, to test the possibility that the ability of anti-mouse IgG to activate B cells may be enhanced by coupling to ferritin, the effect of free ferritin or ferritin coupled to anti-IgM, anti-IgA, or anti-IgG (H+L) on the proliferative response of myoglobin-specific T cells to a wide range of myoglobin concentrations were tested. Ferritin coupled to anti-IgM or anti-IgG (H+L) did not influence the T cell proliferation to the unrelated antigen myoglobin (FIG. 3). Therefore, anti-mouse immunoglobulin was unable to enhance the presentation of an antigen to which it was not coupled.

Figure 4:
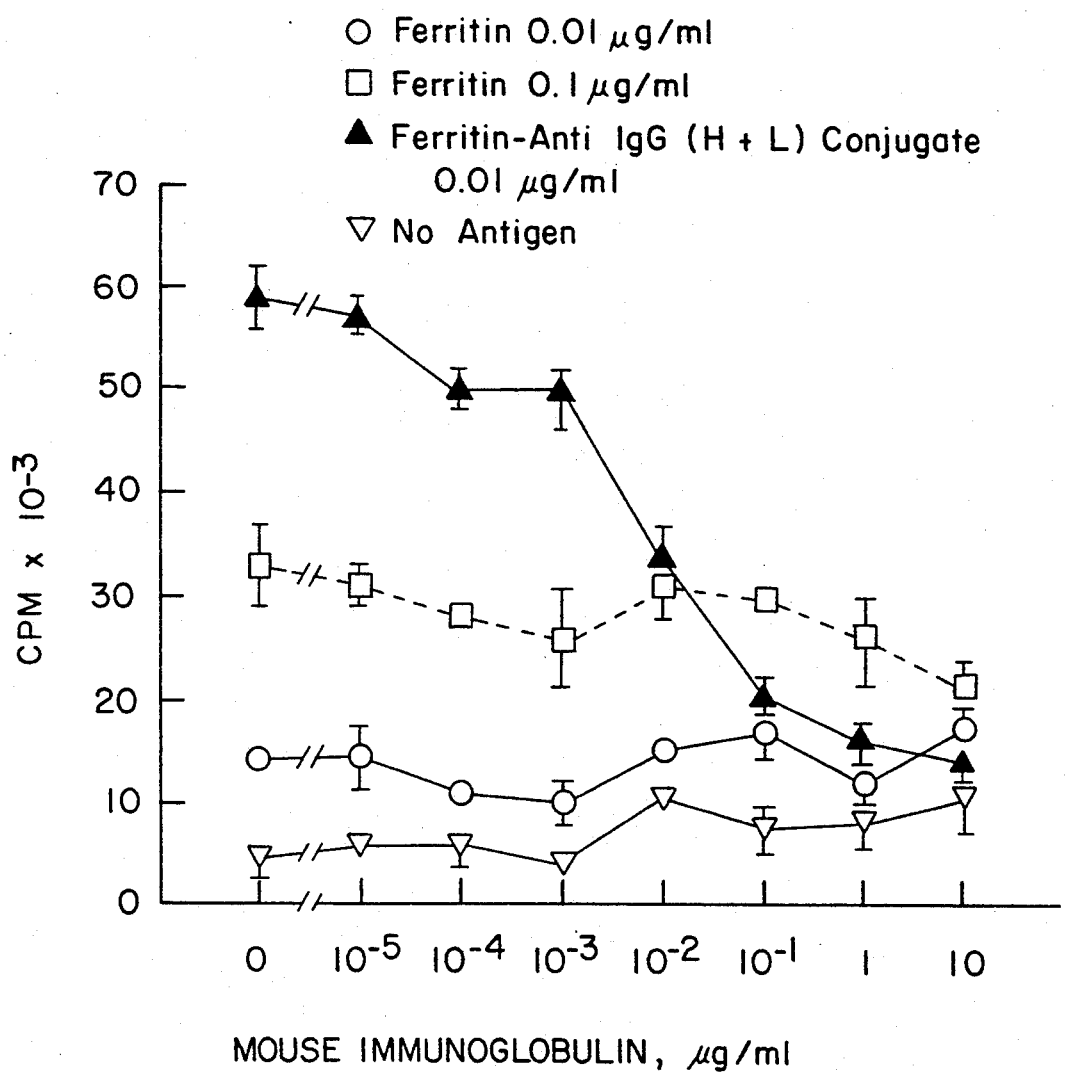
FIG. 4 shows the influence of mouse immunoglobulin on the presentation of ferritin-anti-IgG conjugate. A ferritin-specific T cell line ($5 \times 10^3$/well) was cultured for 4 d with 1000 rad-irradiated spleen cells ($5 \times 10^4$/well) in the presence of 0.01 µg/ml of ferritin (O), 0.1 µg/ml of ferritin (□), 0.01 µg/ml ferritin-anti-IgG (H+L) conjugate (▲), or no antigen (∇), each with mouse immunoglobulin at the concentration indicated on the abscissa. Error bars are SEM of triplicate cultures.

Although lack of effect of ferritin anti-IgA of the same goat immunoglobulin isotype excludes mechanisms involving enhanced uptake by Fc receptors binding the Fc part of the goat Ig, it remained possible that goat anti-IgG or anti-IgM could form immune complexes with mouse Ig secreted or shed by B cells. These complexes might have enhanced uptake through binding of the mouse Fc to Fc receptors. To test for this possibility, the effect of exogenous mouse Ig on the enhancement of antigenic potency by coupling of ferritin to goat anti-IgG (H+L) was tested (FIG. 4). At low antigen dose, where enhancement was seen, there was no increase produced by added mouse Ig over a $10^6$-fold concentration range from $10^{-5}$ to 10 μg/ml, and in the range from $10^{-2}$ to 10 μg/ml, added Ig inhibited the stimulation rather than enhancing it. As a control for nonspecific toxic effects, the mouse Ig had no effect on stimulation by ferritin at either the same or a higher antigen concentration. These results not only rule out Fc receptor uptake as the mechanism of enhancement, but also confirm by competitive inhibition that the mechanism depends on the specificity of the goat antibodies for mouse Ig.

Figure 5:
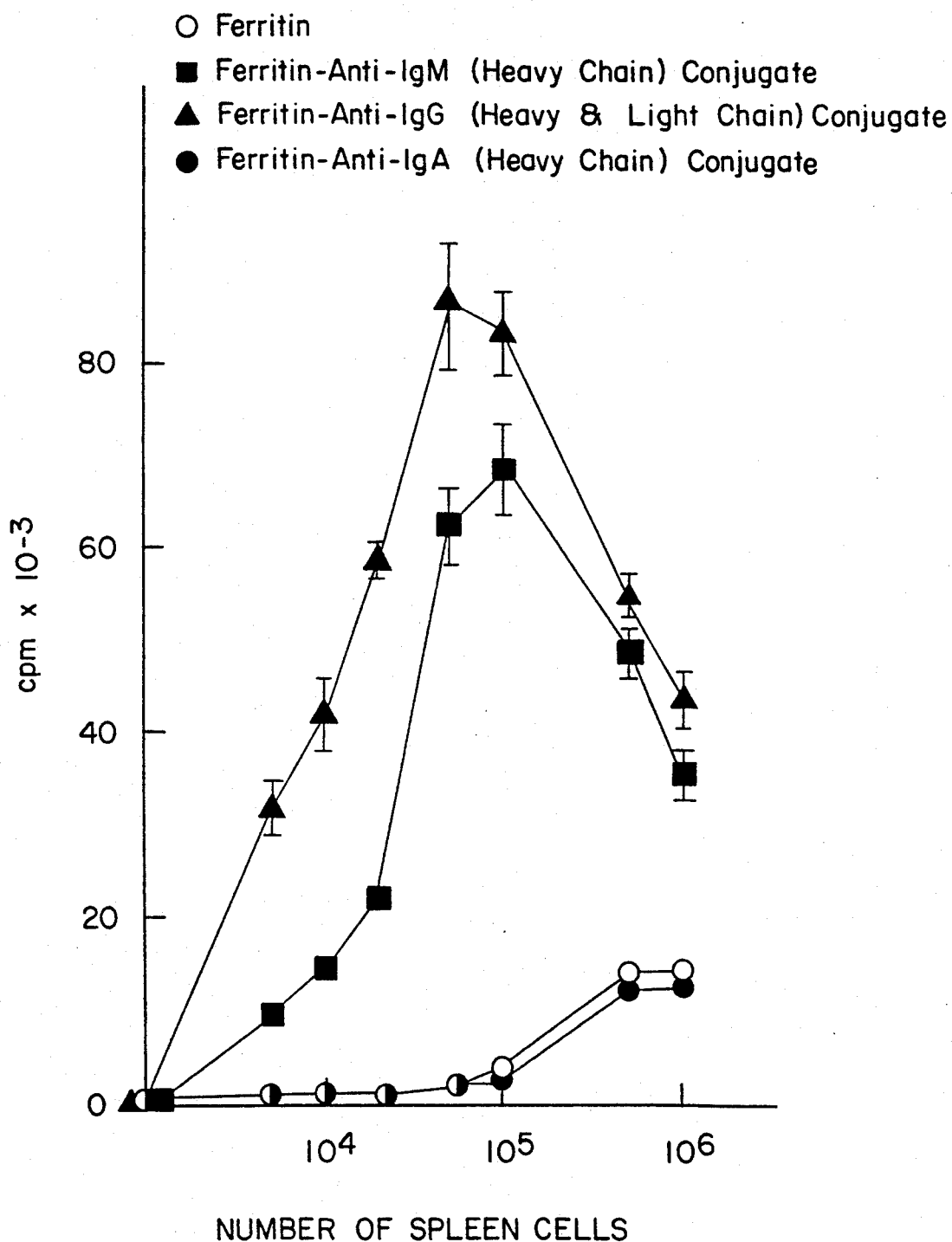
FIG. 5 shows the effect of conjugation of anti-immunoglobulin to ferritin on presenting-cell titration. A ferritin-specific T cell line ($5 \times 10^3$/well) was cultured in the presence of 0.05 μg/ml (ferritin content) of ferritin (○), or ferritin-anti-IgM (H) (■), ferritin-anti-IgG (H+L) (▲), or ferritin-anti-IgA (●) with various numbers of 1000 rad-irradiated spleen cells for 4 d. Error bars are SEM of triplicate cultures.

Increased Efficiency of Presenting Cell Function with Targeted Antigen. FIG. 5 shows the number of spleen cells required for effective antigen presentation to T cells. With ferritin coupled to anti-mouse IgG (H+L) or anti-mouse IgM, the number of spleen cells required either for maximal stimulation or for equal magnitude of stimulation was about 10- to 100-fold lower than that with free ferritin or ferritin coupled to anti-mouse IgA, even though precise quantitative comparison was difficult because of the unparallel nature of the curves and the maximum proliferation was greater with the targeted antigen. This phenomenon may partly be explained by the function of B cells plus SAC instead of SAC alone for presenting cells since the fraction of B cells in unseparated spleen cells is much larger than that of SAC. However, since the ratio of B cells to SAC is less than 100 and the response is enhanced in magnitude as well, the B cells may also present this antigen at low concentration more efficiently on a per cell basis.

The Presentation of Ferritin or Ferritin Coupled to Anti-mouse IgG (H and L) by SAC or B Cells. To confirm that SAC were not participating in the enhancement of presentation of ferritin coupled to anti-mouse IgG (H+L) through another mechanism, such as through Fc receptors, SAC or B cells were enriched and the ability to present ferritin and ferritin coupled to anti-mouse IgG (H+L) were tested. With the SAC-enriched population, ferritin coupled to anti-mouse IgG was presented slightly less efficiently than free ferritin (FIG. 6C). The SAC presentation also was not radiosensitive to 3300 R for either antigen. In contrast, the B cell-enriched population, prepared by passing T-depleted spleen cells three times through Sephadex G-10, displayed more pronounced sensitivity of antigen-presenting function to irradiation, compared to unseparated spleen cells, and the difference in potency between ferritin-anti-Ig and free ferritin was accentuated (compare FIGS. 6A and B). Since Ashwell et al. *J. Exp. Med.* 159:881 (1984) have reported that B cell presentation of antigen is much more radiosensitive than accessory cell (AC) presentation, the radiosensitivity of the enhancement effect and its demonstration in the B cell-enriched population and not the SAC-enriched, B cell-depleted population, both indicate that the presentation of the targeted antigen by whole spleen cells is predominantly due to B cell presentation.

Figure 6:
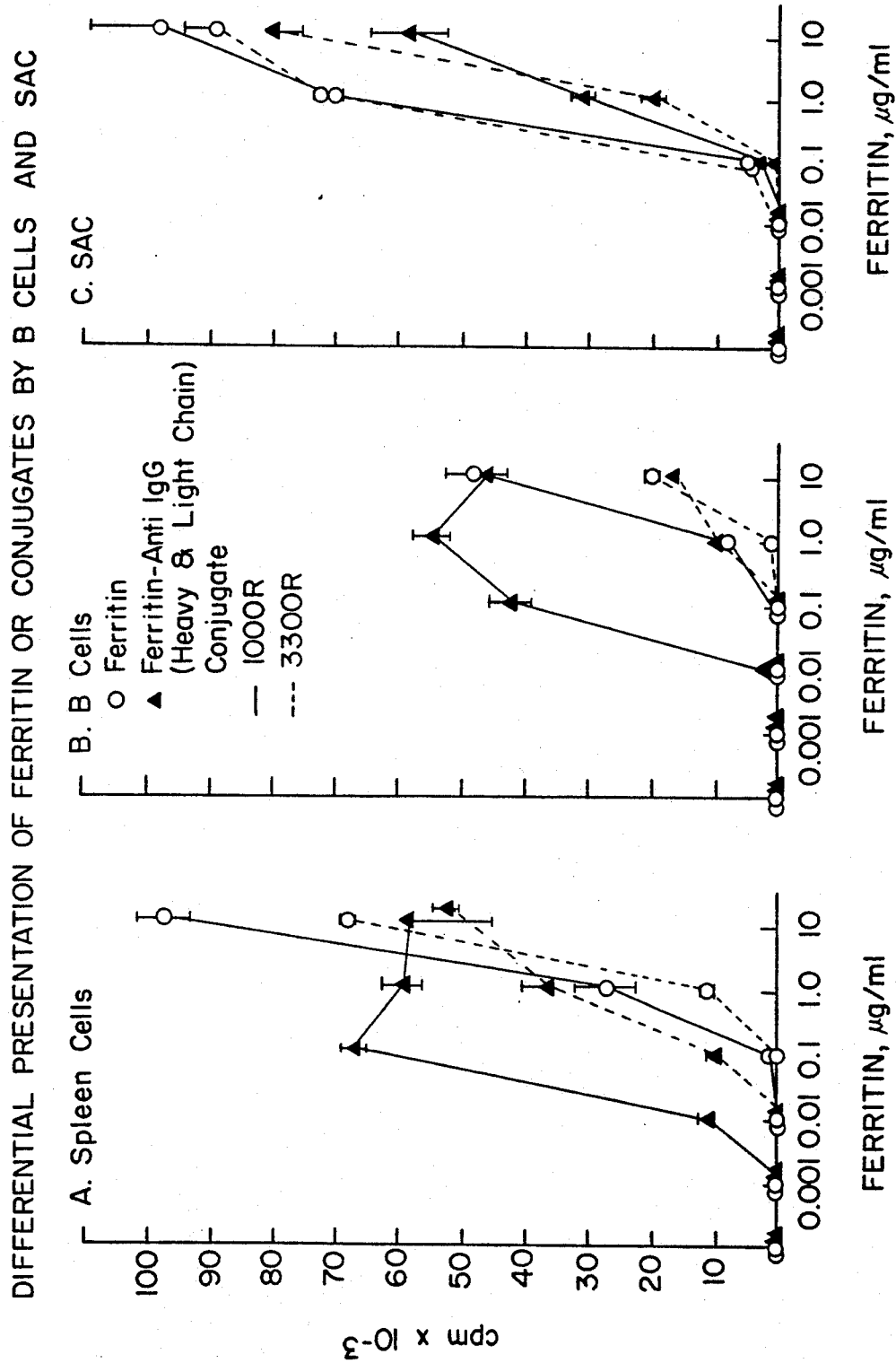
FIGS. 6A-C shows the presentation of ferritin or ferritin-anti-IgG (H+L) to T cells by different subpopulations of spleen cells. A ferritin-specific T cell line ($5 \times 10^3$/well) was cultured in the presence of ferritin (○) or ferritin-anti-IgG (▲) at the indicated concentrations with 1000 rad-(———) or 3300 rad-(-----) irradiated unseparated spleen cells (panel A), glass nonadherent and thrice G-10-column passed T depleted cells (B cells; panel B), or glass-adherent, anti-IgM-coated dish-nonadherent T depleted cells (SAC; panel C) for 4 d. Error bars are SEM of triplicate cultures.
Figure 7:
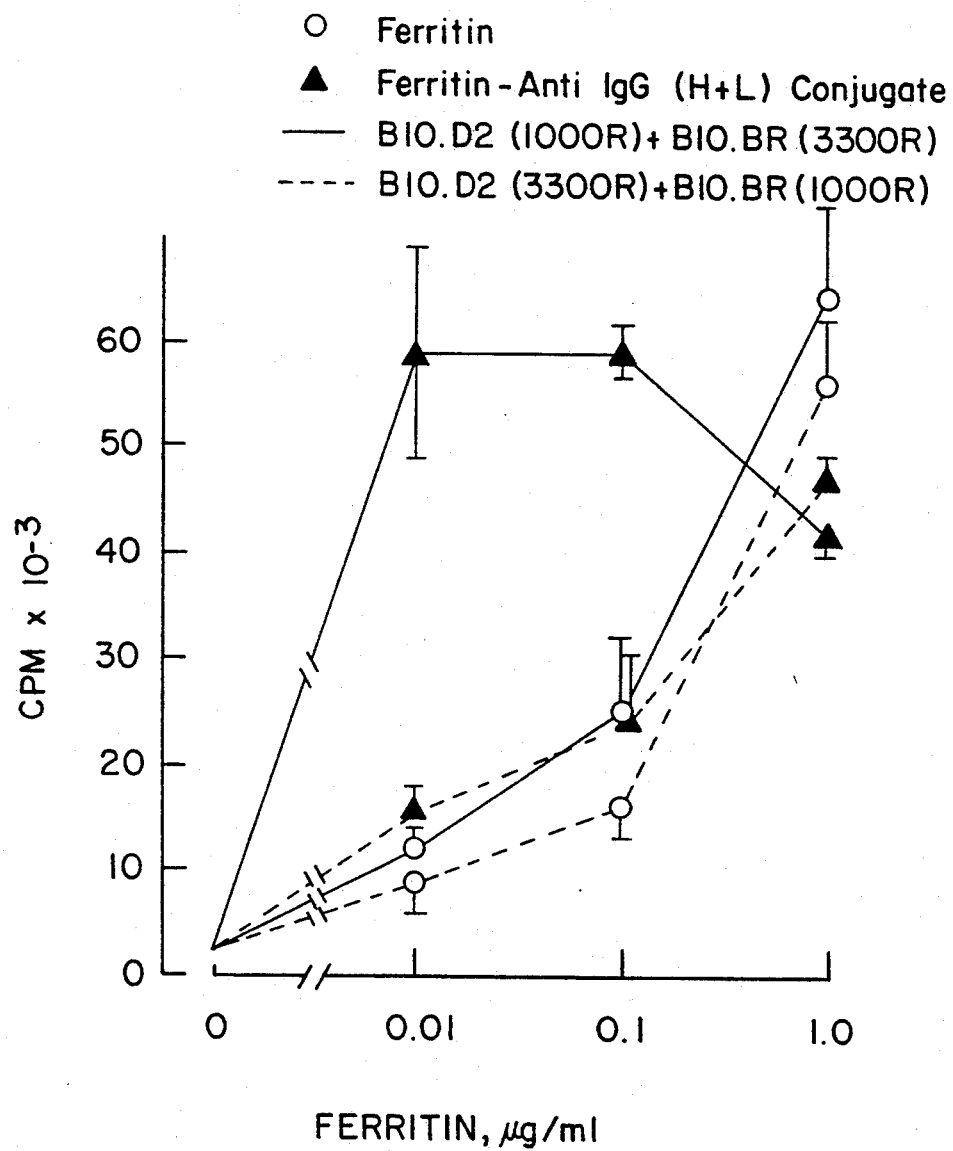
FIG. 7 shows H-2 restriction of enhanced presentation of ferritin-anti-IgG (H+L) by low-dose irradiated spleen cells. A ferritin-specific T cell line ($5 \times 10^3$/well) was cultured for 4 d with the mixture of 1000 rad-irradiated B10.D2 spleen cells ($2.5 \times 10^4$/well) and 3300 rad-irradiated B10.BR spleen cells ($2.5 \times 10^4$/well) (———) or the mixture of 3300 rad-irradiated B10.D2 spleen cells ($2.5 \times 10^4$/well) and 1000 rad-irradiated B10.BR spleen cells ($2.5 \times 10^4$/well) (-----) in the presence of ferritin (○), or ferritin-anti-IgG (H+L) (▲) at the concentration indicated on the abscissa. Error bars are SEM of triplicate cultures. Background without antigen for the former and the latter combination of cells were 3014 cpm and 3137 cpm, respectively, indicating there was not a significant allogeneic effect stimulating the T cell line nonspecifically.

These results demonstrate that the enhancement of antigenic potency for T cell stimulation requires at least a radiosensitive B cell function, which is not affected by depletion of SAC. To ascertain that the B cell itself was the presenting cell, and not another residual accessory cell which had taken up immune complexes shed by B cells, advantage was taken of the genetic restriction of the T cell line and the radiosensitivity of B cell presentation (FIG. 6). The ferritin-specific T cell line is $H-2^d$ restricted, does not respond to ferritin in association with $H-2^k$, and is not alloreactive to $H-2^k$. B10.BR ($H-2^k$) B cells, congenic to B10.D2, should be able to bind the targeted antigen as well as B10.D2 B cells, but cannot present it to the $H-2^d$-restricted T cell line. In the presence of $H-2^d$ SAC, however, if the mechanism involves shedding of immune complexes from B cells and reprocessing and presentation by SAC, the enhancement should still occur. However, if the mechanism requires direct presentation by B cells, then the enhancement should not occur in this mixture. Therefore, 1000 rad-irradiated B10.BR ($H-2^k$) spleen cells were mixed as a source of allogeneic B cells and SAC, with 3300 rad-irradiated B10.D2 spleen cells as a source of functional SAC only, as the 3300 radirradiated B cells did not function in this system (FIG. 6.). No enhancement of the response to ferritin-anti-IgG (H+L) was observed, compared to free ferritin (FIG. 7, dashed curves). As a control, the reverse mixture of 1000 rad-irradiated B10.D2 cells and 3300 rad-irradiated B10.BR cells did mediate the enhancement quite well (FIG. 7, solid curves). The results of FIGS. 6 and 7, taken together, demonstrate that the B cell itself must be the presenting cell for the enhanced presentation of targeted antigen. Further, they confirm that the enhanced presentation is genetically restricted.

Figure 8:
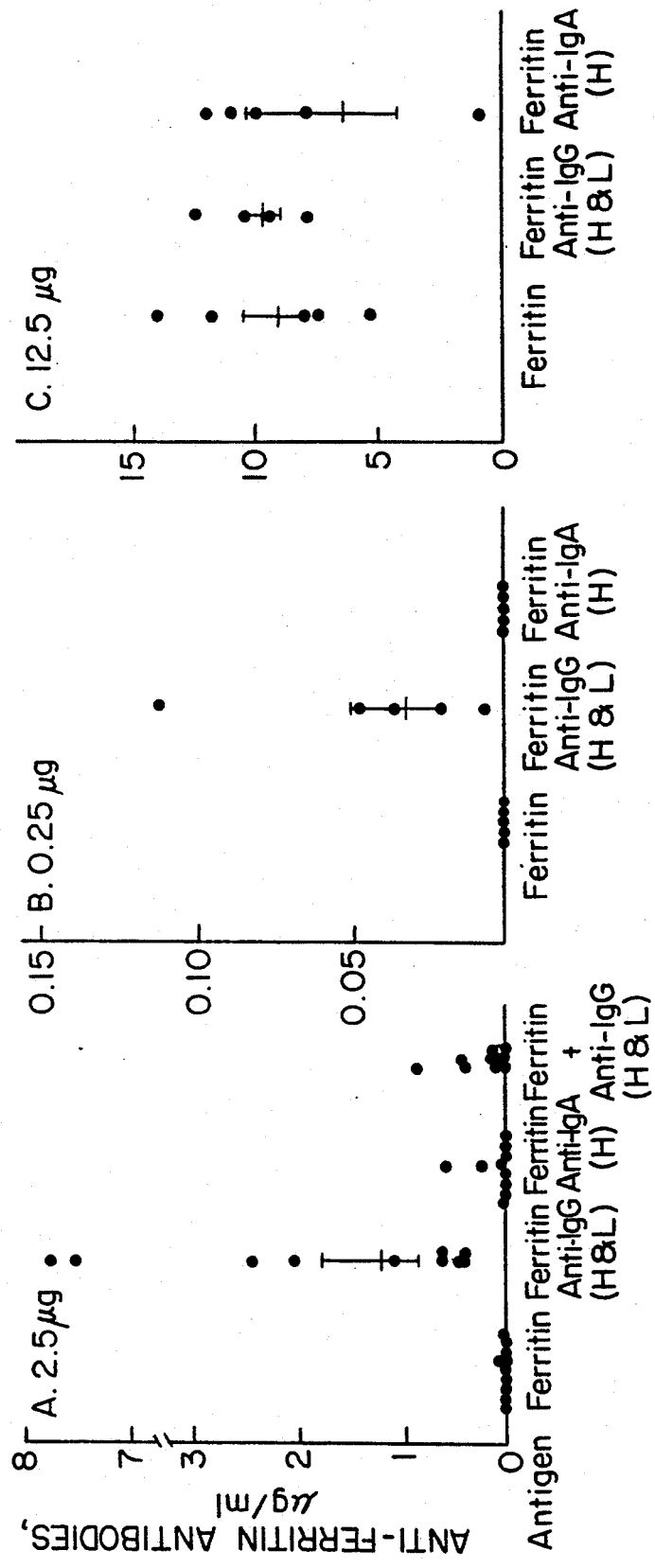
FIGS. 8A-C shows the effect of conjugation with anti-immunoglobulin on the immunogenicity of ferritin in vivo. B10.A mice were immunized with ferritin, ferritin conjugates, or the mixture of ferritin and anti-IgG (H+L) 1:0.1, see FIG. 2 legend) in PBS emulsified 1:1 in incomplete Freund's adjuvant subcutaneously in the tail and bled 10 d later. The concentration of antiferritin antibody in sera was determined by solid phase ELISA. Each point represents the serum antibody concentration from a different mouse, and geometric means and standard errors are indicated with bars (panel A, 10 mice/group; panels B and C, 5 mice/group). The main experiment is in panel A. Panels B and C show that the enhancement holds at a 10-fold lower dose of antigen for immunization, but is not seen at high dose immunization.
Figure 9:
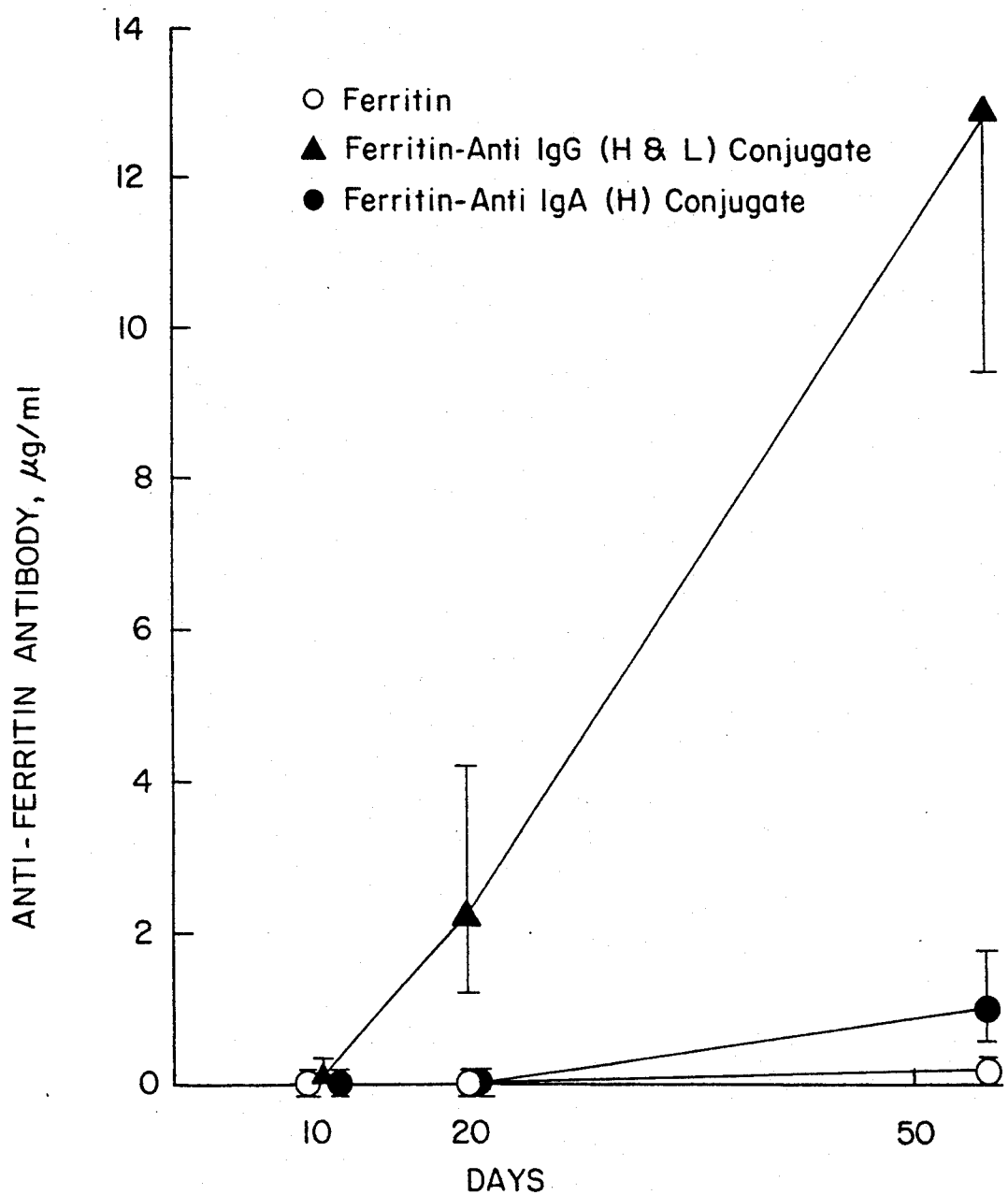
FIG. 9 shows the time course of antibody production to unmodified ferritin or ferritin conjugates in vivo. B10.BR Mice were immunized with 2.5 μg of ferritin (○), ferritin-anti-IgG (H+L) (▲), or ferritin-anti-IgA (●) in PBS emulsified 1:1 in incomplete Freund's adjuvant subcutaneously in the tail and bled on the indicated days. The concentration of antiferritin antibody in each serum sample was determined individually by ELISA. Results represent the geometric means and standard errors for 10 mice in each group.
Figure 10:
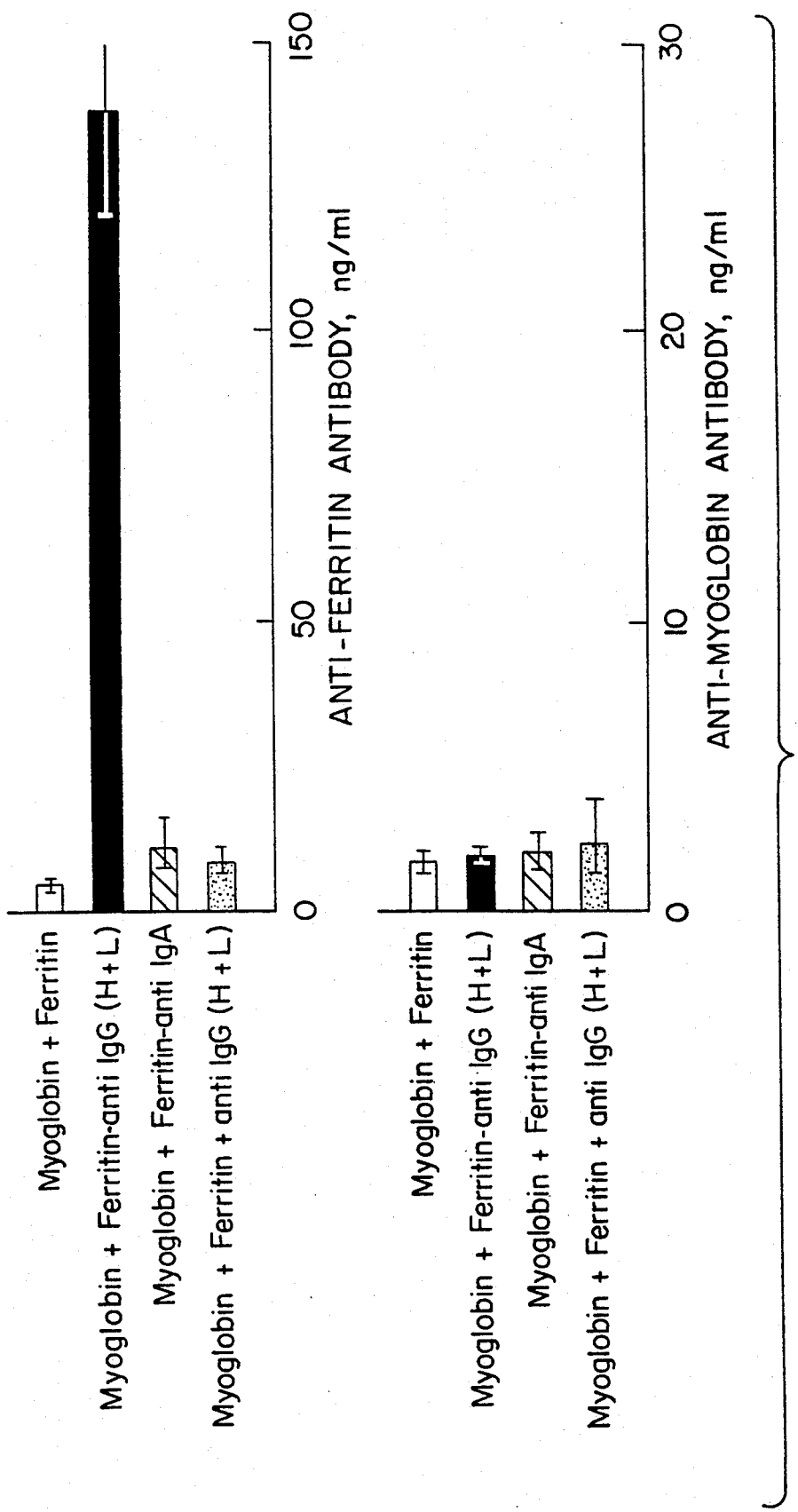
FIG. 10 shows the influence of ferritin conjugates on the antibody response in vivo specific for an unrelated antigen. B10.BR mice were immunized with 1 μg of ferritin, ferritin-anti-IgG (H+L), ferritin-anti-IgA or the mixture of ferritin and anti-IgG (H+L) (1:0.1, see FIG. 2 legend) (concentration based on ferritin content) together with 1 μg of sperm whale myoglobin in PBS emulsified 1:1 in incomplete Freund's adjuvant subcutaneously in the tail and bled 23 d later. The concentration of antiferritin antibody and antimyoglobin antibody in each serum was determined individually by ELISA. Results represent the geometric means and standard errors for 9 mice in each group.

Effect of the Coupling of Antigen to Anti-immunoglobulin Antibodies on Its Immunogenicity for Antibody Production In Vivo. In order to test that the immunogenicity of the antigen molecule by targeting it to the immune system was indeed enhanced in vivo, mice were immunized subcutaneously with free ferritin, ferritin anti-mouse IgA, ferritin-anti-IgG (H+L), or free ferritin mixed with anti-IgG (H+L) antibodies and the serum antibody response to ferritin were measured. In the lower dose range of antigen, ferritin coupled to anti-mouse IgG stimulated the antibody response significantly more than did any of the other antigens (FIG. 8). In FIG. 9 the kinetics of antibody production to ferritin or ferritin conjugates was observed. The effect of coupling ferritin to anti-mouse IgG (H+L) was seen over the entire time course of the response studied. Even on day 10, despite the low responsiveness, there was a significant difference between ferritin-anti-IgG (H+L) (60 ng/ml×2.11) and the two others, namely ferritin (1 ng/ml×1.69, P<0.001) and ferritin-anti-IgA (H) (1 ng/ml×1.8, P<0.001). In order to see whether anti-mouse immunoglobulin stimulated B cells nonspecifically, the total amount of immunoglobulin in the serum was measured. However, there was no increase in total serum immunoglobulin produced by any of these antigens. As a further specificity control, an equivalent small amount of myoglobin was mixed with these antigens to test the effect of ferritin conjugate on the production of antimyoglobin antibodies. No effect was seen (FIG. 10.)

Some of the reasons for selecting immunoglobulin from among many structures in the immune system as the target for directing the antigen are: (a) immunoglobulin receptors on B cells are one place where the antigen binds physiologically, and it has been reported that B cells present antigen to T cells efficiently; (b) since in the whole animal there are many more B cells than AC, when B cells can serve as nonspecific antigen-presenting cells (i.e., present antigen unrelated to their own specificity), the chance of the interaction between T cells and processed antigen plus Ia may be increased; and (c) the fate of antigen which binds to other cell surface structures of AC through antibodies coupled to antigen is not clear. Particularly in the case of H-2 antigens or Fc receptors on B cells, Grey et al. *J. Immunol.* 129:2389 (1982) have shown that the rate of catabolism of rabbit anti-$\beta_2$-microglobulin or immune complexes on B cells is much slower than that of rabbit anti-mouse immunoglobulin antibodies, suggesting that antigen binding to such structures may be processed and presented to T cells less efficiently.

The data presented herein supra, demonstrate that ferritin coupled to goat anti-IgM (H chain specific) or anti-IgG (H+L) antibodies stimulated ferritin-specific T cells to proliferate more than 10-fold more efficiently than free ferritin or ferritin coupled to anti-IgA (H chain) in the presence of unseparated spleen cells as antigen-presenting cells. The anti-IgG presumably bound via its specificity for light chain, whereas the anti-IgA served as a control as few B cells express surface IgA. All three goat antibodies were of the same IgG isotype and coupling ratio. For the reasons mentioned above, the enhancing effect brought about by the coupling of antigen to anti-immunoglobulin due to increased B cell presentation was established.

As a possible explanation one may theorize that the crosslinking of surface immunoglobulin by anti-immunoglobulin antibodies activates B cells, as detected by expression of more surface Ia antigen, by plasma membrane depolarization, and by progression from $G_0$ to $G_1$ in the cell cycle (Mond, et al. *J. Immunol.* 127:881, 1981; Monroe, et al. *J. Exp. Med.* 158:1589, 1983; Howard, et al. *Ann. Rev. Immunol.* 1:307, 1983). In such an activated state, B cells are more efficient at antigen presentation (Kakiuchii, et al. *J. Immunol.* 131:109, 1983) and also are less radio-sensitive. Therefore, it may be suggested that it is possible that ferritin-coupled anti-immunoglobulin antibodies may activate B cells to serve as activated antigen-presenting cells even for antigens not coupled to anti-immunoglobulin antibodies. However, two pieces of evidence indicate that this is not a possible mechanism. First, the mixture of anti-IgG (H+L) antibodies with ferritin did not enhance T cell proliferation as did anti-IgG antibodies coupled to ferritin. The very small enhancement seen even with 10-fold higher amounts of anti-IgG antibodies suggested that activation of B cells by anti-IgG antibodies contributed at most a small part of the effect observed. The second piece of evidence is that ferritin-coupled anti-IgG (H+L) or anti-IgM antibodies did not influence the T cell proliferation to an unrelated antigen, myoglobin.

It may also be argued that it is possible that endocytosis of Ig-coupled ferritin may be more efficient because of its larger size. The fact that ferritin coupled to goat anti-IgA antibodies of the same class and coupling ratio did not show greater immunogenicity excludes this possibility.

Additionally, the negative result with anti-IgA antibodies also showed that the effect is not due to the binding of goat immunoglobulin-coupled ferritin to Fc receptors of B cells or macrophages. Furthermore, since free mouse immunoglobulin in culture diminished rather than increased the enhancing effect of coupling ferritin to anti-IgG (H+L), it is unlikely that the enhancement was due to formation of immune complexes with secreted mouse immunoglobulin which could bind to Fc receptors of B cells or SAC. Moreover, with purified SAC there was no difference in potency between ferritin coupled to anti-IgG antibodies and unmodified ferritin. This suggests that SAC do not play a major role in this enhancement. Furthermore, the lack of observed enhancement when the B cells (1000 rad-irradiated) were allogeneic and the only functional syngeneic presenting cells were SAC (3300 rad-irradiated), indicated that the enhancement was not due to uptake by B cells and then shedding of immune complexes which were actually presented by SAC. For all these reasons, it is clear that the enhancement of antigenic potency in vitro by targeting the antigen is due to increased uptake and genetically restricted presentation by B cells.

Chesnut and Grey *J. Immunol.* 126:1075 (1981) irradiated adherent spleen cells and macrophage-depleted spleen cells with 4500 R and compared their ability to present rabbit immunoglobulin or rabbit anti-mouse immunoglobulin antibodies to T cells from rabbit immunoglobulin immunized mice. The 4500 rad-irradiated macrophage-depleted spleen cells could present rabbit anti-mouse immunoglobulin antibodies but not rabbit immunoglobulin to T cells. In contrast to this, Ashwell et al. *J. Exp. Med.* 159:881 (1984) showed that a radiation dose of as little as 1500 R significantly reduced the antigen-presenting capability of small resting B cells, and doses of over 2000 R totally abrogated it. They suggested that in the study by Chesnut and Grey, rabbit anti-immunoglobulin antibodies activated the B cells and made them radioresistant as antigen-presenting cells. The results of the present radiosensitivity tests are compatible with the study by Ashwell et al. *J. Exp. Med.* 159:881 (1984), but different from that by Chesnut and Grey, supra. Since the dose of anti-mouse immunoglobulin antibodies per antigen-presenting cell in the present study is more than 1000-fold lower than that used by Chesnut and Grey, supra, it might not be enough to activate B cells and make them radioresistant as antigen-presenting cells.

In the antibody response to ferritin in vivo, at low doses, ferritin coupled to anti-mouse IgG (H+L) antibodies was significantly more immunogenic than free ferritin, ferritin coupled to anti-IgA (H chain), or free ferritin plus anti-mouse IgG (H+L) antibodies. The mechanism of this effect can be explained based on the in vitro experiments. B cells in regional lymph nodes may take up ferritin coupled to anti-IgG antibodies more efficiently and stimulate a larger number of ferritin-specific T cells. The resulting T cells presumably help B cells to make more anti-ferritin antibodies. The negative result with control antigens such as ferritin coupled to anti-IgA and the mixture of ferritin and anti-IgG, and the specificity control with myoglobin, supported this interpretation in the same way as for the in vitro experiments.

The possibility of a "side-effect" in which B cells presenting ferritin to T cells may be activated by these T cells at the same time and secrete immunoglobulin nonspecifically was also examined but no increase in total serum immunoglobulin was detectable.

Another possible mechanism involving the classical carrier effect of immunoglobulin coupled to ferritin should also be considered. Ferritin-specific B cells binding ferritin coupled to immunoglobulin may present processed immunoglobulin as well as processed ferritin. Those B cells may be helped by both ferritin-specific T cells and goat immunoglobulin-specific T cells. However, such a mechanism ought to be independent of the specificity of the goat immunoglobulin. Since ferritin coupled to goat anti-IgG (H+L) antibodies stimulated antibody production much more than ferritin coupled to goat anti-IgA antibodies of the same isotype (which were no better than free ferritin), this is not likely to be a primary mechanism.

Therefore, although an operative mechanism cannot be defined as definitively in vivo as in vitro, the most likely explanation of the enhanced immunogenicity in vivo, is the targeting of the antigen to B cells as antigen-presenting cells, which, because of their greater numbers and the increased affinity to binding via the anti-immunoglobulin antibody, increase the efficacy of antigen presentation to helper T cells. Then increased help results in increased antibody production.

It should also be considered as to why free immunoglobulin did not inhibit the effect of anti-IgG antibodies coupled to ferritin in vivo, although in the in vitro T cell proliferation tests, addition of mouse immunoglobulin did inhibit the enhancing effect of anti-IgG antibodies coupled to ferritin. It is possible that at the site where B cells interact with antigen in emulsion in Freund's adjuvant (e.g., in the lymph nodes), the local concentration of immunoglobulin may be lower than in serum. However, it is also possible that free immunoglobulin does diminish the effect of anti-IgG antibodies coupled to ferritin and that the in vivo effect would be even greater without this competition. The underlying factors are not known at this time.

Although the observations made supra do not clarify the possible mechanisms as to how targeting the antigen works in vivo, the important point is that it does work in vivo. The minimum dose of ferritin for successful immunization is reduced 10- to 50-fold by targeting it with anti-Ig. For immunization, particularly to viruses, various attempts are being made to prepare synthetic vaccines. Since synthetic vaccines are small peptides, which usually consist of six to twenty amino acids, they are usually poorly immunogenic because (a) they may not have epitopes for both B cells and T cells, (b) they may have a short half-life because of renal excretion, and (c) they may not be taken up by antigen-presenting cells efficiently. For immunization with synthetic vaccines, several different carriers have been used with varying results. The present invention now makes it possible, regardless of the exact mechanism, to employ anti-immunoglobulin as a much more effective carrier than conventional carriers and renders immunization with synthetic vaccines much more feasible in most cases. The targeting approach of the present invention also makes it possible to produce antibodies to antigens available in only very limited quantities.

It is understood that the examples and embodiments described herein are for illustrative purposes only and that various modifications or changes in light thereof will be suggested to persons skilled in the art and are to be included within the spirit and purview of this application and the scope of the appended claims.

We claim:

1. An immune response stimulating composition comprising an immunogenic amount effective to stimulate enhanced in vivo antibody production to an antigen, of a conjugate of said antigen coupled to an anti-immunoglobulin antibody that binds to B-cell surface immunoglobulins.

2. A method for stimulating an enhanced in vivo antibody production to an antigen, which comprises administering to a host an immunologically effective amount of a conjugate of said antigen coupled to an anti-immunoglobulin antibody that binds to B-cell surface immunoglobulins.

3. The method according to claim 2, wherein said anti-immunoglobulin antibody is a member selected from the group consisting of anti-IgG, anti-IgM and anti-IgD antibodies.

4. The method according to claim 3, wherein said anti-immunoglobulin antibody is a monoclonal antibody.

5. The method according to claim 3, wherein said antibody is specific for heavy or light chain immunoglobulin.

6. The method according to claim 2, wherein said antigen is selected from the group consisting of ferritin and myoglobin.

7. The method according to claim 6, wherein said antigen is ferritin.

8. The method according to claim 6, wherein said antigen is myoglobin.

9. The method according to claim 2, wherein said conjugate of said antigen coupled to said anti-immunoglobulin antibody is a conjugate of ferritin to anti-IgM.

10. The method according to claim 2, wherein said conjugate of said antigen coupled to said anti-immunoglobulin antibody is a conjugate of ferritin to anti-IgG.

11. The method according to claim 2, wherein said binding of said conjugate to said surface immunoglobulins of said B-cells results in increased presentation of said antigen by said B-cells to helper T-cells.

12. The method according to claim 11, wherein said increased presentation of said antigen by said B-cells to said helper T-cells results in activation of said helper T-cells, and wherein said activated helper T-cells activate B-cells to produce antibody to said antigen.

13. The method according to claim 2, wherein said binding of said conjugate to said surface immunoglobulins of said B-cells occurs with nonspecific B-cells.

14. The method for stimulating an enhanced in vivo antibody production to an antigen, which comprises administering to a host an immunologically effective amount of a conjugate of said antigen coupled to an anti-IgG antibody or an anti-IgM antibody.

15. A method for stimulating an enhanced in vivo antibody production to an antigen, which comprises administering to a host an immunologically effective amount of a conjugate of said antigen coupled to an anti-immunoglobulin antibody that has a high affinity for the Ig receptors of B-cells.

* * * * *